(12) United States Patent
Wong et al.

(10) Patent No.: US 6,794,168 B1
(45) Date of Patent: Sep. 21, 2004

(54) PROCESS FOR OXIDISING AROMATIC COMPOUNDS

(75) Inventors: Luet Lok Wong, Oxford (GB); Jonathan Peter Jones, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 10/018,730

(22) PCT Filed: Jun. 19, 2000

(86) PCT No.: PCT/GB00/02379

§ 371 (c)(1),
(2), (4) Date: Apr. 4, 2002

(87) PCT Pub. No.: WO00/78973

PCT Pub. Date: Dec. 28, 2000

(30) Foreign Application Priority Data

Jun. 18, 1999 (GB) .............................................. 9914373

(51) Int. Cl.$^7$ .............................. C12N 9/02; C12P 7/00; C12P 21/06; C07K 1/00
(52) U.S. Cl. ...................... 435/189; 435/132; 435/69.1; 530/402
(58) Field of Search ................................ 435/189, 132, 435/69.1; 530/402; 536/23.2, 259.3, 320.1

(56) References Cited

U.S. PATENT DOCUMENTS

| | | | |
|---|---|---|---|
| 5,763,237 A | | 6/1998 | Savithiry et al. ........... 435/148 |
| 6,100,074 A | * | 8/2000 | Flitsch et al. ............... 435/189 |

FOREIGN PATENT DOCUMENTS

| | | |
|---|---|---|
| EP | 334841 | 9/1993 |
| GB | 2294692 | 8/1996 |
| GB | 2306485 | 7/1997 |
| WO | WO 88/01641 | 3/1988 |
| WO | WO 94/01564 | 1/1994 |
| WO | WO 96/14419 | 5/1996 |
| WO | WO 97/16553 | 5/1997 |
| WO | WO 00/31273 | 6/2000 |

OTHER PUBLICATIONS

Bogaards et al., "Human Cytochrome P450 Enzyme Selectivities in the Oxidation of Chlorinated Benzenes,"Toxicology and Applied Pharmacology 132, 44–52.
Gotoh, Osamu, "Substrate Recognition Sites in Cytochrome P450 Family 2 (CYP2) Proteins Inferred from Comparative Analyses of Amino Acid and Coding Nucleotide Sequences," J. Biol. Chem 267, 83–90.
Mueller, et al., "Twenty Five Years of P450cam Research," CytoChrome P450: Structure, Mechanism and Biochemistry:2nd Ed. Ortiz de Montellano Ed., Plenum Press, New York 1995, pp. 83–124.
Shimoji et al (1998), *Design of a Novel P450: A Functional Bacterial–Human cytochrome P450*Biochemistry 37, 8848–52.
Gooch et al (1989), *Effects of ortho– and Non–ortho–Substituted Polychlorinated Biphenyl Congeners on the Hepatic Monooxygenase System in Scup (Stenotomus chrysops)*, Toxicol. Appl. Pharmacol. 98, 422–33.
England et al (1998), *the oxidation of naphthalene and pyrene by cytochrome P450$_{cam}$*, FEBS Letters 424, 271–4.
Jones et al (2000), *The oxidation of polychlorinated benezenes by genetically engineered cytochrome P450$_{cam}$: potential applications in bioremediation* Chem. Commun. 3, 247–8.
Hegg et al (1999), *Herbicide–Degrading α–Keto Acid–Dependent Enzyme TfdA: Metal Coordination Environment and Mechanistic Insights*, Biochemistry 38, 16714–26.
Nickerson et al (1997), *The catalytic activity of cytochrome P450$_{cam}$ towards styrene oxidation is increased by site–spcific mutagenesis*, FEBS Letters 405,153–6.
Jones et al (1996), *Engineering the selectivity of aliphatic C–H bond oxidation catalysed by cytochrome P450$_{com}$*, Chem. Communications 21, 2413–4.
Tuck et al (1993), *Active Sites of the Cytochrome p450$_{cam}$ (CYP101) F89787W and F87A Mutants*, J. Biol. Chem. 268, 269–75.
Filipovic et al (1992), *Ethylbenzene Hydroxylation by Cytochrome P450cam*, Biochemical and Biophysical Research Communications, 189,488–95.
Dong et al (1996, *Coexpression of Mammalian Cytochrome P450 and Reductase in Escherichia coli*, Archives of Biochemistry and Biophysics 327, 254–9.
Atkins et al (1989), *Molecular Recognition in Cytochrome P–450: Alteration of Regioselective Alkane Hydroxylation via Protein Engineering*, J. Am. Chem. Soc. 111, 2715–7.
White et al (1984), *Regioselectivity in the Cytochromes P–450: Control by Protein Constraints and by Chemical Reactivities* Archives of Biochemistry and Biophysics 228, 493–502.
Loida et al (1993), *Molecular Recognition in Cytochrome P–450: Mechanism for the Control of Uncoupling Reactions*, Biochemistry 32, 11530–8.
Di Primo et al (1990), *Mutagenesis of a Single Hydrogen Bond in Cytochrome P–450 Alters Cation Binding and Heme Solvation*, J. Biol. Chem. 265, 5631–3.
Sibbesen et al (1996), *Putidaredoxin Reductase–Putadaredoxin–Cytochrome P450 cam Triple Fusion Protein*, J. Biol. Chem. 271, 22462–22469.
Oliver et al (1997), *A Single Mutation in Cytochrome P450 BM3 Changes Substrate Orientation in a Catalytic Intermediate and the Regiospecificity of Hydroxylation*, Biochemistry 36, 1567–72.
Atkins et al (1988), *The Roles of Active Site Hydrogen Bonding in Cytochrome P–450 cam as Revealed by Site–directed Mutagenesis*, J. Biol. Chem. 263, 18842–9.

\* cited by examiner

*Primary Examiner*—Tekchand Saidha
(74) *Attorney, Agent, or Firm*—Fulbright & Jaworski, L.L.P.

(57) ABSTRACT

Process of oxidising a substrate which is a halo aromatic compound, which process comprises oxidizing said substrate with a monooxygenase enzyme. The enzyme may be P450cam. The process may be carried out in cells, animals or plants.

3 Claims, No Drawings

SEQUENCE LISTING

<160> NUMBER OF SEQ ID NOS: 18

<210> SEQ ID NO 1
<211> LENGTH: 1242
<212> TYPE: DNA
<213> ORGANISM: Pseudomonas putida

<400> SEQUENCE: 1

```
acgactgaaa ccatacaaag caacgccaat cttgcccctc tgccacccca tgtgccagag      60
cacctggtat tcgacttcga catgtacaat ccgtcgaatc tgtctgccgg cgtgcaggag     120
gcctgggcag ttctgcaaga atcaaacgta ccggatctgg tgtggactcg ctgcaacggc     180
ggacactgga tcgccactcg cggccaactg atccgtgagg cctatgaaga ttaccgccac     240
ttttccagcg agtgcccgtt catccctcgt gaagccggcg aagcctacga cttcattccc     300
acctcgatgg atccgcccga gcagcgccag tttcgtgcgc tggccaacca agtggttggc     360
atgccggtgg tggataagct ggagaaccgg atccaggagc tggcctgctc gctgatcgag     420
```

-continued

```
agcctgcgcc cgcaaggaca gtgcaacttc accgaggact acgccgaacc cttcccgata    480
cgcatcttca tgctgctcgc aggtctaccg aagaagata tcccgcactt gaaataccta     540
acggatcaga tgacccgtcc ggatggcagc atgaccttcg cagaggccaa ggaggcgctc    600
tacgactatc tgataccgat catcgagcaa cgcaggcaga agccgggaac cgacgctatc    660
agcatcgttg ccaacggcca ggtcaatggg cgaccgatca ccagtgacga agccaagagg    720
atgtgtggcc tgttactggt cggcggcctg gatacggtgg tcaatttcct cagcttcagc    780
atggagttcc tggccaaaag cccggagcat cgccaggagc tgatcgagcg tcccgagcgt    840
attccagccg cttgcgagga actactccgg cgcttctcgc tggttgccga tggccgcatc    900
ctcacctccg attacgagtt tcatggcgtg caactgaaga aggtgaccaa gatcctgcta    960
ccgcagatgc tgtctggcct ggatgagcgc gaaaacgcct gcccgatgca cgtcgacttc   1020
agtcgccaaa aggtttcaca caccaccttt ggccacggca gccatctgtg ccttggccag   1080
cacctggccc gccgggaaat catcgtcacc ctcaaggaat ggctgaccag gattcctgac   1140
ttctccattg ccccgggtgc ccagattcag cacaagagcg gcatcgtcag cggcgtgcag   1200
gcactccctc tggtctggga tccggcgact accaaagcgg ta                      1242
```

<210> SEQ ID NO 2
<211> LENGTH: 414
<212> TYPE: PRT
<213> ORGANISM: Pseudomonas putida

<400> SEQUENCE: 2

```
Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Tyr
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
    130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Arg Gln Lys Pro Gly Thr Asp Ala Ile Ser Ile Val Ala
    210                 215                 220

Asn Gly Gln Val Asn Gly Arg Pro Ile Thr Ser Asp Glu Ala Lys Arg
```

```
                225                 230                 235                 240
Met Cys Gly Leu Leu Leu Val Gly Gly Leu Asp Thr Val Val Asn Phe
                    245                 250                 255
Leu Ser Phe Ser Met Glu Phe Leu Ala Lys Ser Pro Glu His Arg Gln
                260                 265                 270
Glu Leu Ile Glu Arg Pro Glu Arg Ile Pro Ala Ala Cys Glu Glu Leu
            275                 280                 285
Leu Arg Arg Phe Ser Leu Val Ala Asp Gly Arg Ile Leu Thr Ser Asp
        290                 295                 300
Tyr Glu Phe His Gly Val Gln Leu Lys Lys Gly Asp Gln Ile Leu Leu
305                 310                 315                 320
Pro Gln Met Leu Ser Gly Leu Asp Glu Arg Glu Asn Ala Cys Pro Met
                325                 330                 335
His Val Asp Phe Ser Arg Gln Lys Val Ser His Thr Thr Phe Gly His
                340                 345                 350
Gly Ser His Leu Cys Leu Gly Gln His Leu Ala Arg Arg Glu Ile Ile
            355                 360                 365
Val Thr Leu Lys Glu Trp Leu Thr Arg Ile Pro Asp Phe Ser Ile Ala
        370                 375                 380
Pro Gly Ala Gln Ile Gln His Lys Ser Gly Ile Val Ser Gly Val Gln
385                 390                 395                 400
Ala Leu Pro Leu Val Trp Asp Pro Ala Thr Thr Lys Ala Val
                405                 410

<210> SEQ ID NO 3
<211> LENGTH: 3150
<212> TYPE: DNA
<213> ORGANISM: Bacillus megaterium

<400> SEQUENCE: 3
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aagcgcttaa atttgtacgt     240
gattttgcag agacggggtt atttacaagc tggacgcatg aaaaaaattg gaaaaaagcg     300
cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgatacaa ttggtctttg cggctttaac     480
tatcgcttta acagctttta ccgagatcag cctcatccat ttattacaag tatggtccgt     540
gcactggatg aagcaatgaa caagctgcag cgagcaaatc cagacgaccc agcttatgat     600
gaaaacaagc gccagtttca gaagatatc aaggtgatga cgacctagt agataaaatt     660 attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtcttt tatcatttgc gctgtatttc     840
ttagtgaaaa atccacatgt attacaaaaa gcagcagaag aagcagcacg agttctagta     900
gatcctgctc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa ggcgacgaac taatggttct gattcctcag    1080
```

| cttcaccgtg ataaaacaat ttggggagac gatgtggaag agttccgtcc agagcgtttt | 1140 |
| gaaaatccaa gtgcgattcc gcagcatgcg tttaaaccgt ttggaaacgg tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctggata ttaagaaaac tttaacgtta | 1320 |
| aaacctgaag ctttgtggt aaaagcaaaa tcgaaaaaaa ttccgcttgg cggtattcct | 1380 |
| tcacctagca ctgaacagtc tgccaaaaaa gcacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |
| ccgcctgata acgcaaagca atttgtcgac tggttagacc aagcgtctgc tgatgaagta | 1680 |
| aaaggcgttc gctactccgt atttggatgc ggcgataaaa actgggctac tacgtatcaa | 1740 |
| aaagtgcctg cttttatcga tgaaacgctt gccgctaaag gggcagaaaa catcgctgac | 1800 |
| cgcggtgaag cagatgcaag cgacgacttt gaaggcacat atgaagaatg cgtgaacat | 1860 |
| atgtggagtg acgtagcagc ctactttaac ctcgacattg aaaacagtga agataataaa | 1920 |
| tctactcttt cacttcaatt tgtcgacagc gccgcggata tgccgcttgc gaaaatgcac | 1980 |
| ggtgcgtttt caacgaacgt cgtagcaagc aaagaacttc aacagccagg cagtgcacga | 2040 |
| agcacgcgac atcttgaaat tgaacttcca aaagaagctt cttatcaaga aggagatcat | 2100 |
| ttaggtgtta ttcctcgcaa ctatgaagga atagtaaacc gtgtaacagc aaggttcggc | 2160 |
| ctagatgcat cacagcaaat ccgtctggaa gcagaagaag aaaaattagc tcatttgcca | 2220 |
| ctcgctaaaa cagtatccgt agaagagctt ctgcaatacg tggagcttca agatcctgtt | 2280 |
| acgcgcacgc agcttcgcgc aatggctgct aaaacggtct gcccgccgca taagtagag | 2340 |
| cttgaagcct tgcttgaaaa gcaagcctac aaagaacaag tgctggcaaa acgtttaaca | 2400 |
| atgcttgaac tgcttgaaaa atacccggcg tgtgaaatga aattcagcga atttatcgcc | 2460 |
| cttctgccaa gcatacgccc gcgctattac tcgatttctt catcacctcg tgtcgatgaa | 2520 |
| aaacaagcaa gcatcacggt cagcgttgtc tcaggagaag cgtggagcgg atatggagaa | 2580 |
| tataaaggaa ttgcgtcgaa ctatcttgcc gagctgcaag aaggagatac gattacgtgc | 2640 |
| tttatttcca caccgcagtc agaatttacg ctgccaaaag accctgaaac gccgcttatc | 2700 |
| atggtcggac cgggaacagg cgtcgcgccg tttagaggct ttgtgcaggc gcgcaaacag | 2760 |
| ctaaaagaac aaggacagtc acttggagaa gcacatttat acttcggctg ccgttcacct | 2820 |
| catgaagact atctgtatca agaagagctt gaaaacgccc aaagcgaagg catcattacg | 2880 |
| cttcataccg cttttctcg catgccaaat cagccgaaaa catacgttca gcacgtaatg | 2940 |
| gaacaagacg gcaagaaatt gattgaactt cttgatcaag gagcgcactt ctatatttgc | 3000 |
| ggagacggaa gccaaatggc acctgccgtt gaagcaacgc ttatgaaaag ctatgctgac | 3060 |
| gttcaccaag tgagtgaagc agacgctcgc ttatggctgc agcagctaga gaaaaaggc | 3120 |
| cgatacgcaa aagacgtgtg ggctgggtaa | 3150 |

<210> SEQ ID NO 4
<211> LENGTH: 1049
<212> TYPE: PRT
<213> ORGANISM: Bacillus megaterium

<400> SEQUENCE: 4

Met Thr Ile Lys Glu Met Pro Gln Pro Lys Thr Phe Gly Glu Leu Lys

```
1               5                   10                  15
Asn Leu Pro Leu Leu Asn Thr Asp Lys Pro Val Gln Ala Leu Met Lys
            20                  25                  30
Ile Ala Asp Glu Leu Gly Glu Ile Phe Lys Phe Glu Ala Pro Gly Arg
            35                  40                  45
Val Thr Arg Tyr Leu Ser Ser Gln Arg Leu Ile Lys Glu Ala Cys Asp
    50                  55                  60
Glu Ser Arg Phe Asp Lys Asn Leu Ser Gln Ala Leu Lys Phe Val Arg
65                  70                  75                  80
Asp Phe Ala Gly Asp Gly Leu Phe Thr Ser Trp Thr His Glu Lys Asn
                85                  90                  95
Trp Lys Lys Ala His Asn Ile Leu Leu Pro Ser Phe Ser Gln Gln Ala
                100                 105                 110
Met Lys Gly Tyr His Ala Met Met Val Asp Ile Ala Val Gln Leu Val
            115                 120                 125
Gln Lys Trp Glu Arg Leu Asn Ala Asp Glu His Ile Glu Val Pro Glu
    130                 135                 140
Asp Met Thr Arg Leu Thr Leu Asp Thr Ile Gly Leu Cys Gly Phe Asn
145                 150                 155                 160
Tyr Arg Phe Asn Ser Phe Tyr Arg Asp Gln Pro His Pro Phe Ile Thr
                165                 170                 175
Ser Met Val Arg Ala Leu Asp Glu Ala Met Asn Lys Leu Gln Arg Ala
            180                 185                 190
Asn Pro Asp Asp Pro Ala Tyr Asp Glu Asn Lys Arg Gln Phe Gln Glu
            195                 200                 205
Asp Ile Lys Val Met Asn Asp Leu Val Asp Lys Ile Ile Ala Asp Arg
    210                 215                 220
Lys Ala Ser Gly Glu Gln Ser Asp Asp Leu Leu Thr His Met Leu Asn
225                 230                 235                 240
Gly Lys Asp Pro Glu Thr Gly Glu Pro Leu Asp Asp Glu Asn Ile Arg
                245                 250                 255
Tyr Gln Ile Ile Thr Phe Leu Ile Ala Gly His Glu Thr Thr Ser Gly
                260                 265                 270
Leu Leu Ser Phe Ala Leu Tyr Phe Leu Val Lys Asn Pro His Val Leu
            275                 280                 285
Gln Lys Ala Ala Glu Glu Ala Ala Arg Val Leu Val Asp Pro Ala Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
                340                 345                 350
Glu Leu Met Val Leu Ile Pro Gln Leu His Arg Asp Lys Thr Ile Trp
            355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
```

```
Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
        450                 455                 460

Glu Gln Ser Ala Lys Lys Ala Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
        530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
        610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
        690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
        770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845
```

-continued

```
Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys  Gly Asp Gly Ser Gln  Met Ala Pro
        995                 1000                 1005

Ala Val  Glu Ala Thr Leu Met  Lys Ser Tyr Ala Asp  Val His Gln
    1010                 1015                 1020

Val Ser  Glu Ala Asp Ala Arg  Leu Trp Leu Gln Gln  Leu Glu Glu
    1025                 1030                 1035

Lys Gly  Arg Tyr Ala Lys Asp  Val Trp Ala Gly
    1040                 1045
```

```
<210> SEQ ID NO 5
<211> LENGTH: 51
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(51)
<223> OTHER INFORMATION:

<400> SEQUENCE: 5
gagattaaga attcataaac acatgggagt gcgtgccata tgaacgcaaa c            51

<210> SEQ ID NO 6
<211> LENGTH: 7
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(7)
<223> OTHER INFORMATION:

<400> SEQUENCE: 6

Thr Asp Gly Gly Ser Ser Ser
1               5

<210> SEQ ID NO 7
<211> LENGTH: 36
<212> TYPE: DNA
<213> ORGANISM: Artificial sequence
<220> FEATURE:
<223> OTHER INFORMATION: Desired coding sequence
```

```
<220> FEATURE:
<221> NAME/KEY: misc_feature
<222> LOCATION: (1)..(36)
<223> OTHER INFORMATION:

<400> SEQUENCE: 7
gaactgagta gtgccactga cggaggatcc tcatcg                              36

<210> SEQ ID NO 8
<211> LENGTH: 5
<212> TYPE: PRT
<213> ORGANISM: Artificial sequence
<220> FEATURE:
<223> OTHER INFORMATION: Desired coding sequence
<220> FEATURE:
<221> NAME/KEY: MISC_FEATURE
<222> LOCATION: (1)..(5)
<223> OTHER INFORMATION:

<400> SEQUENCE: 8

Thr Asp Gly Gly Ser
1               5

<210> SEQ ID NO 9
<211> LENGTH: 36
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(36)
<223> OTHER INFORMATION:

<400> SEQUENCE: 9
cgatgaggat cctccgtcag tggcactact cagttc                              36

<210> SEQ ID NO 10
<211> LENGTH: 36
<212> TYPE: DNA
<213> ORGANISM: Artificial sequence
<220> FEATURE:
<223> OTHER INFORMATION: Desired coding sequence
<220> FEATURE:
<221> NAME/KEY: misc_feature
<222> LOCATION: (1)..(36)
<223> OTHER INFORMATION:

<400> SEQUENCE: 10
tcatcgggat cctcatcgat gtctaaagta gtgtat                              36

<210> SEQ ID NO 11
<211> LENGTH: 4
<212> TYPE: PRT
<213> ORGANISM: Artificial sequence
<220> FEATURE:
<223> OTHER INFORMATION: Desired coding sequence
<220> FEATURE:
<221> NAME/KEY: MISC_FEATURE
<222> LOCATION: (1)..(4)
<223> OTHER INFORMATION:

<400> SEQUENCE: 11

Gly Ser Ser Ser
1

<210> SEQ ID NO 12
<211> LENGTH: 52
<212> TYPE: DNA
```

```
<213> ORGANISM: Artificial sequence
<220> FEATURE:
<223> OTHER INFORMATION: Desired coding sequence
<220> FEATURE:
<221> NAME/KEY: misc_feature
<222> LOCATION: (1)..(52)
<223> OTHER INFORMATION:

<400> SEQUENCE: 12
cccgataggc aatggtaatc atcgggagtc tagagcatcg aagctttcat cg        52

<210> SEQ ID NO 13
<211> LENGTH: 52
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(52)
<223> OTHER INFORMATION:

<400> SEQUENCE: 13
cgatgaaagc ttcgatgctc tagactcccg atgattacca ttgcctatcg gg        52

<210> SEQ ID NO 14
<211> LENGTH: 24
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(24)
<223> OTHER INFORMATION:

<400> SEQUENCE: 14
tcatcgacgc gtcgcgaact gctg                                       24

<210> SEQ ID NO 15
<211> LENGTH: 69
<212> TYPE: DNA
<213> ORGANISM: Artificial sequence
<220> FEATURE:
<223> OTHER INFORMATION: Desired coding sequence
<220> FEATURE:
<221> NAME/KEY: misc_feature
<222> LOCATION: (1)..(69)
<223> OTHER INFORMATION:

<400> SEQUENCE: 15
cccgataggc aatggtaagt aggtgaatat ctaatcccca tctatgcgcg agtggagtct    60
agagttcga                                                         69

<210> SEQ ID NO 16
<211> LENGTH: 21
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(21)
<223> OTHER INFORMATION:

<400> SEQUENCE: 16
tcatcgaagc ttggctgttt t                                          21
```

```
<210> SEQ ID NO 17
<211> LENGTH: 47
<212> TYPE: DNA
<213> ORGANISM: Artificial sequence
<220> FEATURE:
<223> OTHER INFORMATION: Desired coding sequence
<220> FEATURE:
<221> NAME/KEY: misc_feature
<222> LOCATION: (1)..(47)
<223> OTHER INFORMATION:

<400> SEQUENCE: 17
acaatttcac acaggatcta gaccatatgt catcgaagct ttcatcg         47

<210> SEQ ID NO 18
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(47)
<223> OTHER INFORMATION:

<400> SEQUENCE: 18
cgatgaaagc ttcgatgaca tatggtctag atcctgtgtg aaattgt         47
```

PROCESS FOR OXIDISING AROMATIC COMPOUNDS

The invention relates to a process for enzymatically oxidizing halogenated aromatic compounds.

Chlorinated aromatic compounds such as the chlorobenzene and polychlorinated biphenyls (PCBs) are among the most wide-spread organic contaminants in the environment due to their common application as solvents, biocides, and in the heavy electrical industry. They are also some of the most problematic environmental pollutant, not only because of the health hazards (lipid solubility and hence accumulation in fatty tissues, toxicity and carcinogenicity) but also because of their slow degradation in the environment.

Whilst microorganisms have shown extraordinary abilities to adapt and evolve to degrade most of the organic chemicals released into the environment, the most chemically inert compounds such as PCBs do persist for two main reasons. First, these compounds have very low solubility in water and therefore their bioavailability is low. Research into this problem has focussed on the use of detergents and other surfactants to enhance their solubility and bioavailability. Second, these compounds require activation by enzymatic oxidation or reduction, and it can take a long time for the necessary genetic adaptations by microorganisms to occur, and even then the organisms may not be stable and viable.

We have now found, according to the present invention, that a monoxygenase, in particular $P450_{cam}$ and its physiological electron transfer partners putidaretoxin and putidaretoxin reductase, can be used to oxidise halogenated aromatic compounds. Also mutants of the monoxygenase with substitutions in the active site have enhanced oxidation activity. Thus suitable monoxygenases can be expressed in microorganisms, animals and plants which are going to be used to oxidise the halogenated aromatic compounds.

Accordingly the present invention provides a process for oxidizing a substrate which is a halo aromatic compound, which process comprises oxidizing said substrate with a monooxygenase enzyme.

The process may be carried out in a cell that expresses:
(a) the enzyme
(b) an electron transfer reductase; and
(c) an electron transfer redoxin The halo aromatic compound is typically a benzene or biphenyl compound. The benzene ring is optionally fused and can be substituted. The halogen is typically chlorine. In many cases there is more than one halogen atom in the molecule, typically 2 to 5 or 6, for example 3. Generally 2 of the halogen atoms will be ortho or para to one another. The compound may or may not contain an oxygen atom such as a hydroxy group, an aryloxy group or a carboxy group. The compound may or may not be chlorophenol or a chlorophenoxyacetic compound.

Specific compounds which can be oxidised by the process of the present invention include 1,2; 1,3- and 1,4-dichlorobenzene, 1,2,4; 1,2,3- and 1,3,5-trichlorobenzene, 1,2,4,5- and 1,2,3,5-tetrachlorobenzene, pentachlorobenzene, hexachlorobenzene, 3,3'-dichlorobiphenyl and 2,3, 4,5,6- and 2,2',4,5,5'-pentachlorobiphenyl.

Other compounds which can be oxidised by the process include recalcitrant halo aromatic compounds, especially dioxins and halogenated dibenzofurans, and the corresponding compounds where one or both oxygen atoms is/are replaced by sulphur, in particular compounds of the formula:

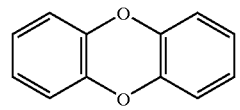

which possess at least one halo substituent, such as dioxin itself, 2,3,7,8-tetrachlorodibenzioxin.

The oxidation typically gives rise to 1,2 or more oxidation products. These oxidation products will generally comprise 1 or more hydroxyl groups. Generally, therefore, the oxidation products are phenols which can readily be degraded. It is particularly noteworthy that pentachlorobenzene and hexachlorobenzene can be oxidised in this way since they are very difficult to degrade. In contrast the corresponding phenols can be readily degraded by a variety of Pseudomonas and other bacteria. The atom which is oxidized is generally a ring carbon.

The enzyme is typically a natural monooxygenase or a mutant thereof. The natural monooxygenase is generally a prokaryotic or eukaryotic enzyme. Typically it is a haem-containing enzyme and/or a P450 enzyme. The monooxygenase may or may not be a TfdA (2,4-dichlorophenoxy) acetate/α-KG dioxygenase. The monooxygenase is generally of microorganism (e.g. bacterial), fungal, yeast, plant or animal origin, typically of a bacterium of the genus Pseudomonas. These organisms are typically soil, fresh water or salt water dwelling. In the case of a mutant monooxygenase the non-mutant form may or may not be able to oxidize the substrate.

The monooxygenase typically has a coupling efficiency of at least 1%, such as at least 2%, 4%, 6% or more. The monooxygenase typically has a product formation rate of at least 5 $min^{-1}$, such as at least 8, 10, 15, 20, 25, 50, 100, 150 $min^{-1}$ or more. The coupling efficiency or product formation rate is typically measured using any of the substrates or conditions mentioned herein. Thus they are typically measured in the in vitro conditions described in Example 2, in which case the relevant monooxygenase, reductase and redoxin would be present instead of, but at the same concentration as, $P450_{cam}$, putidaretoxin reductase and putidaretoxin.

The mutant typically has at least one mutation in the active site. A preferred mutant comprises a substitution of an amino acid in the active site by an amino acid with a less polar side chain. Thus the amino acid is typically substituted with an amino acid which is above it in Table 1.

TABLE 1

HYDROPATHY SCALE FOR AMINO ACID SIDE CHAINS

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |

TABLE 1-continued

HYDROPATHY SCALE FOR AMINO ACID SIDE CHAINS

| Side Chain | Hydropathy |
|---|---|
| Gln | −3.5 |
| Asp | −3.5 |
| Asn | −3.5 |
| Lys | −3.9 |
| Arg | −4.5 |

An amino acid 'in the active site' is one which lines or defines the site in which the substrate is bound during catalysis or one which lines or defines a site through which the substrate must pass before reaching the catalytic site. Therefore such an amino acid typically inateracts with the substrate during entry to the catalytic site or during catalysis. Such an interaction typically occurs through an electrostatic interaction (between charged or polar groups), hydrophobic interaction, hydrogen bonding or van der Waals forces.

The amino acids in the active site can be identified by routine methods to those skilled in the art. These methods include labelling studies in which the enzyme is allowed to bind a substrate which modifies ('labels') amino acids which contact the substrate. Alternatively the crystal structure of the enzyme with bound substrate can be obtained in order to deduce the amino acids in the active site.

The monooxygenase typically has 1, 2, 3, 4 or more other mutations, such as substitutions, insertions or deletions. The other mutations may be in the active site or outside the active site. Typically the mutations are in the 'second sphere' residues which affect or contact the position or orientation of one or more of the amino acids in the active site. The insertion is typically at the N and/or C terminal and thus the enzyme may be part of a fusion protein. The deletion typically comprises the deletion of amino acids which are not involved in catalysis, such as those outside the active site. The monooxygenase may thus comprise only those amino acids which are required for oxidation activity.

The other mutations in the active site typically alter the position and/or conformation of the substrate when it is bound in the active site. The mutation may make the site on the substrate which is to be oxidized more accessible to the haem group. Thus the mutation may be a substitution to an amino acid which has a smaller or larger, or more or less polar, side chain.

The other mutations typically increase the stability of the protein, or make it easier to purify the protein. They typically prevent the dimerisation of the protein, typically by removing cysteine residues from the protein (e.g. by substitution of cysteine at position 334 of $P450_{cam}$, or at an equivalent position in a homologue, preferably to alanine). They typically allow the protein to be prepared in soluble form, for example by the introduction of deletions or a poly-histidine tag, or by mutation of the N-terminal membrane anchoring sequence. The mutations typically inhibit protein oligomerisation, such as oligomerisation arising from contacts between hydrophobic patches on protein surfaces.

Typically the mutant monoxygenase is at least 70% homologous to a natural monooxygenase on the basis of amino acid identity.

Any of the homologous proteins mentioned herein are typically at least 70% homologous to a protein or at least 80 or 90% and more preferably at least 95%, 97% or 99% homologous thereto over at least 20, preferably at least 30, for instance at least 40, 60 or 100 or more contiguous amino acids. The contiguous amino acids may include the active site. This homology may alternatively be measured not over contiguous amino acids or nucleotides but over only the amino acids in the active site.

The monoxygenase is preferably:
(i) $P450_{cam}$,
(ii) a naturally occurring homologue of (i),
(iii) a mutant of (i) or (ii).

Typically (i) is any allelic variant of $P450_{cam}$ of *Pseudomonas putida* (e.g. of the polypeptide sequence shown in SEQ ID No. 2). Typically (ii) is a species homologue of (i) which has sequence homology with (i), and is typically $P450_{BM-3}$ of *Bacillus megaterium* (e.g. the polypeptide sequence shown in SEQ ID No. 4 and the nucelotide sequence is shown in SEQ ID NO: 3), $P450_{terp}$ of *Pseudomonas sp*, $P450_{eryF}$ of *Saccharopollyspora erythraea*, or P450 105 D1 (CYP105) of *Streptomyces griseus* strains.

The active site of (ii) or (iii) may be substantially the same as the active site of (i) or any of the mutants of (i) mentioned herein. Thus the site may comprise the same amino acids in substantially the same positions.

Typically in (iii) amino acid 96 of $P450_{cam}$, or the equivalent amino acid in a homologue, has been changed to an amino acid with a less polar side chain.

The 'equivalent' side chain in the homologue is one at the homologous position. This can be deduced by lining up the $P450_{cam}$ sequence and the sequence of the homologue based on the homology between the two sequences. The PILEUP, BLAST and BESTFIT algorithms can be used to line up the sequences (for example as described in Altschul S. F. (1993) J Mol Evol 36:290–300; Altschul, S, F et al (1990) J Mol Biol 215:403–10 and (Devereux et al (1984) Nucleic Acids Research 12, p387–395)). These algorithms can also be used to calculate the levels of homology discussed herein (for example on their default settings). The equivalent amino acid will generally be in a similar place in the active site of the homologue as amino acid 96 in $P450_{cam}$.

The discussion below provides examples of the positions at which substitutions may be made in $P450_{cam}$. The same substitutions may be made at equivalent positions in the homologues. Standard nomenclature is used to denote the mutations. The letter of the amino acid present in the natural form is followed by the position, followed by the amino acid in the mutant. To denote multiple mutations in the same protein each mutation is listed separated by hyphens. The mutations discussed below using this nomenclature specify the natural amino acid in $P450_{cam}$, but it is to be understood that the mutation could be made to a homologue which has a different amino acid at the equivalent position.

An additional mutation is typically an amino acid substitution at amino acid 87, 98, 101, 185, 244, 247, 248, 296, 395, 396 or a combination of these, for example as shown in table 2.

The following combinations of substitutions are preferred:
(i) Substitution at position 87 to amino acids of different side-chain volume, such as substitutions (typically of F) to A, L, I and W, combined with substitutions at position 96 to amino acids of different side-chain volume such as (typically Y to) A, L, F, and W. These combinations alter the space available in the upper part of the substrate pocket compared to the wild-type enzyme, for example, from Y96W-F87W (little space) to Y96A-F87A (more space), as well as the location of the space, for example from one side in Y96F-F87A to the other in Y96A-F87W.

(ii) Substitution at position 96 to F combined with substitutions at positions 185 and 395. Both T185 and I395 are at the upper part of the substrate pocket, and substitution with A creates more space while substitution with F will reduce the space available and push the substrate close to the haem.

(iii) Substitutions at position 96 to A, L, F, and W combined with substitutions at residues closer to the haem including at 101, 244, 247, 295, 296 and 396 to A, L, F, or W. These combinations will create or reduce space in the region of the different side-chains to offer different binding orientations to substrates of different sizes. For example, the combinations Y96W-L244A and Y96L-V247W will offer very different pockets for the binding of the substrate.

(iv) Triple substitutions at combinations of positions 87, 96, 244, 247, 295, 296, 395 and 396 with combinations of A, L, F, and W. The aim is to vary the size and shape of the hydrophobic substrate binding pocket. For example, the Y96A-F87A-L244A combination creates more space compared to the Y96F-F87W-V396L combination, thus allowing larger substrates to bind to the former while restricting the available binding orientations of smaller substrates in the latter. The combinations Y96F-F87W-V247L and Y96F-F87W-V295I have comparable substrate pocket volumes, but the locations of the space available for substrate binding are very different. The combination Y96F-F87L-V247A has a slightly larger side-chain volume at the 96 position than the combination Y96L-F87L-V247A, but the L side-chain at the 96 position is much more flexible and the substrate binding orientations will be different for the two triple mutants.

(v) The mutants with four or five substitutions were designed with similar principles of manipulating the substrate volume, the different flexibility of various side-chains, and the location of the space available in the substrate pocket for substrate binding so as to effect changes in selectivity of substrate oxidation.

Mutations are generally introduced into the enzyme by using methods known in the art, such as site directed mutagenesis of the enzyme, PCR and gene shuffling methods or by the use of multiple mutagenic oligonucleotides in cycles of site-directed mutagenesis. Thus the mutations may be introduced in a directed or random manner. Typically the mutagenesis method produces one or more polynucleotides encoding one or more different mutants. In one embodiment a library of mutant oligonucleotides is produced which can be used to produce a library of mutant enzymes.

The process is typically carried out in the presence of the natural cofactors of the monooxygenase. Thus typically in addition to the enzyme (a) and the substrate the process is carried out in the presence of an electron transfer reductase (b), an electron transfer redoxin (c), cofactor for the enzyme and an oxygen donor. In this system the flow of electrons is generally: cofactor→(b)→(c)→(a).

(b) is generally an electron transfer reductase which is able to mediate the transfer of electrons from the cofactor to (c), such as a naturally occurring reductase or a protein which has homology with a naturally occurring reductase, such as at least 70% homology, or a fragment of the reductase or homologue. (b) is typically a reductase of any of the organisms mentioned herein, and is typically a flavin dependent reductase, such as putidaredoxin reductase.

(c) is generally an electron transfer redoxin which is able to mediate the transfer of electrons from the cofactor to (a) via (b). (c) is typically a naturally occurring electron transfer redoxin or a protein which has homology with a naturally occuring electron transfer redoxin, such as at least 70% homology; or a fragment of the redoxin or homologue. (c) is typically a redoxin of any of the organisms mentioned herein. (c) is typically a two-iron/two sulphur redoxin, such as putidaredoxin.

The cofactor is any compound capable of donating an electron to (b), such as NADH. The oxygen donor is any compound capable of donating oxygen to (a), such as dioxygen.

Typically (a), (b) and (c) are present as separate proteins; however they may be present in the same fusion protein. Typically only two of them, preferably (b) and (c), are present in the fusion protein. Typically these components are contiguous in the fusion protein and there is no linker peptide present.

Alternatively a linker may be present between the components. The linker generally comprises amino acids that do not have bulky side chains and therefore do not obstruct the folding of the protein subunits. Preferably the amino acids in the linker are uncharged. Preferred amino acids in the linker are glycine, serine, alanine or threonine. In one embodiment the linker comprises the sequence N-Thr-Asp-Gly-Gly-Ser-Ser-Ser-C (SEQ ID NO:6). The linker is typically from at least 5 amino acids long, such as at least 10, 30 or 50 or more amino acids long.

In the process the concentration of (a), (b) or (c) is typically from $10^{-8}$ to $10^{-2}$M, preferably from $10^{-6}$ to $10^{-4}$M. Typically the ratio of concentrations of (a):(b) and/or (a):(c) is from 0.1:01 to 1:10, preferably from 1:0.5 to 1:2, or from 1:0.8 to 1:1.2. Generally the process is carried out at a temperature and/or pH at which the enzyme is functional, such as when the enzyme has at least 20%, 50%, 80% or more of peak activity. Typically the pH is from 3 to 11, such as 5 to 9 or 6 to 8, preferably 7 to 7.8 or 7.4. Typically the temperature is 10 to 90° C., such as 25 to 75° C. or 30 to 60° C.

In the process different monooxygenases may be present. Typically each of these will be able to oxidise different substrates, and thus using a mixture of monooxygenases will enable a wider range of substrates to be oxidised.

In one embodiment the process is carried out in the presence of a substance able to remove hydrogen peroxide by-product (e.g. a catalase).

In one embodiment the process is carried out in the presence of the enzyme, substrate and an oxygen atom donor, such as hydrogen peroxide or t-butylhydroperoxide, for example using the peroxide shunt.

In one embodiment in the process the (a), (b) and (c) together are typically in a substantially isolated form and/or a substantially purified form, in which case together they will generally comprise at least 90%, e.g., at least 95%, 98% or 99% of the protein in the preparation.

The process may be carried out inside or outside a cell. The cell is typically in culture, at a locus, in vivo or in planta (these aspects are discussed below).

The process is typically carried out at a locus such as in land (e.g in soil) or in water (e.g, fresh water or sea water). When it carried out in culture the culture typically comprises different types of cells of the invention, for example expressing different monooxygenases of the invention. Generally such cells are cultured in the presence of assimible carbon and nitrogen sources.

Typically the cell in which the process is carried out is one in which the monooxygenase does not naturally occur. In another embodiment the monooxygenase is expressed in a cell in which it does naturally occur, but at higher levels than naturally occurring levels. The cell may produce 1, 2, 3, 4 or more different monooxygenases of the invention. These monoxygenases may be capable of oxidizing different halo aromatic compounds. Typically the cell also expresses any of the reductases and/or redoxins discussed above.

The cell is typically produced by introducing into a cell (i.e. transforming the cell with) a vector comprising a polynucleotide that encodes the monooxygenase. The vector may integrate into the genome of the cell or remain extra-chromosomal. The cell may develop into the animal or plant discussed below. Typically the coding sequence of the polynucleotide is operably linked to a control sequence which is capable of providing for the expression of the coding sequence by the host cell. The control sequence is generally a promoter, typically of the cell in which the monooxygenase expressed.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

The vector is typically a transposon, plasmid, virus or phage vector. It typically comprises an origin of replication. It typically comprises one or more selectable marker genes, for example an ampicillin resistance gene in the case of a bacterial plasmid. The vector is typically introduced into host cells using conventional techniques including calcium phosphate precipitation, DEAE-dextran transfection, or electroporation.

Components (b) and (c) may be expressed in the cell in a similar manner. Typically (a), (b) and (c) are expressed from the same vector, or may be expressed from different vectors. They may be expressed as three different polypeptides. Alternatively they may be expressed in the form of fusion proteins. The cell typically expresses more than one type of monooxygenase.

In one embodiment the three genes encoding the three proteins of the $P450_{cam}$ system, i.e. camA, camB, and camC are placed in the mobile regions of standard transposon vectors and incorporated into the genome of Pseudomonas and flavobacteria. Alternatively plasmid vectors for expressing these genes may used, in which case the $P450_{cam}$ gene cluster will be extra-chromosomal.

The cell may be prokaryotic or eukaryotic and is generally any of the cells or of any of the organisms mentioned herein. Preferred cells are Pseudomanas, flavobacteria or fungi cells (e.g. Aspergillus). In one embodiment the cell is one which in its naturally occurring form is able to oxidise any of the substrates mentioned herein. Typically the cell is in a substantially isolated form and/or substantially purified form, in which case it will generally comprise at least 90%, e.g. at least 95%, 98% or 99% of the cells or dry mass of the preparation.

The invention provides a transgenic animal or plant whose cells are any of the cells of the invention. The animal or plant is transgenic for the monooxygenase gene and typically also an appropriate electron transfer reductase and/or redoxin gene. They may be homozygote or heterozygote for such genes, which are typically transiently introduced into the cells, or stably integrated (e.g. in the genome). The animal is typically a worm (e.g earthworm) or nematode. The plant or animal may be obtained by transforming an appropriate cell (e.g. embryo stem cell, callus or germ cell), fertilising the cell if required, allowing the cell to develop into the animal or plant and breeding the animal or plant true if required. The animal or plant may be obtained by sexual or asexual (e.g cloning) propagation of an animal or plant of the invention or of the F1 organism (or any generation removed from the F1, or the chimera that develops from the transformed cell).

As discussed above the process may be carried out at a locus. Thus the invention also provides a method of treating a locus contaminated with a halo aromatic compound comprising contacting the locus with a monooxygenase, cell, animal or plant of the invention. These organisms are then typically allowed to oxidise the halo aromatic compound. In one embodiment the organisms used to treat the locus are native to the locus. Thus they may be obtained from the locus (e.g. after contamination), transformed/transfected (as discussed above) to express the monooxygenase (and optionally an appropriate electron transfer reductase and/or redoxin.

In one embodiment the locus is treated with more than one type of organism of the invention, e.g. with 2, 3, 4, or more types which express different monooxygenases which oxidise different halo aromatic compounds. In one embodiment such a collection of organisms between them is able to oxidise all halobenzenes, e.g. all chlorobenzenes.

The organisms (e.g. in the form of the collection) may carry out the process of the invention in a bioreactor (e.g. in which they are present in immobilised form). Thus the water or soil to be treated may be passed through such a bioreactor. Soil may be washed with water augmented with surfactants or ethanol and then introduced into the bioreactor.

The invention also provides a process for selecting a mutant of a monooxygenase for its ability to oxidise any of the substrates mentioned herein, which process comprises screening a library of said mutants for their oxidation effect on the substrate. Thus typically the substrate is provided to the library and mutants are selected based on their ability to oxidise the substrate, for example at a particular rate or under particular conditions. The mutant may be selected based on its ability to oxidise the substrate to a particular oxidation product.

Typically the library will be in the form of cells which comprise the mutant enzymes. Generally each cell will express only one particular mutant enzyme. The library typically comprises at least 500 mutants, such as at least 1,000 or 5,000 mutants, preferably at least 10,000 different mutants.

The library typically comprises a random population of mutants. The library may undergo one or more rounds of selection whilst being produced and therefore may not comprise a random population.

The library is typically produced by contacting any of the cells discussed herein which expresses the monooxygenase with a mutagen and/or when the cell is a mutator cell culturing the cell in conditions in which mutants are produced. The mutagen may be contacted with the cell prior to or during culturing of the cell. Thus the mutagen may be present during replication of the cell or replication of the genome of the cell.

The mutagen generally causes random mutations in the polynucleotide sequence which encodes (a). The mutagen is typically a chemical mutagen, such as nitrosomethyguanidine, methyl- or ethylmethane sulphonic acid, nitrite, hydroxylamine, DNA base analogues, and acridine dyes, such as proflavin. It is typically electromagnetic radiation, such as ultra-violet radiation at 260 nm (absorption maximum of DNA) and X-rays. It is typically ionising radiation.

A mutator cell is generally deficient in one or more of the primary DNA repair pathways (such as *E. Coli* pathways mutS, mutD or mutT, or their equivalents in another organism), and thus has a high mutation rate. Simply culturing such cell leads to the DNA encoding (a) to become mutated. The cell may be of *E. Coli* XL1 Red mutator strain.

The mutant selected from the library may be used in any aspect of the invention, thus it may be used to oxidise a substrate in the process of the invention or may be expressed in the cell, animal or plant of the invention. It may be used in the method of treating a locus.

The invention is also illustrated by the Examples:

EXAMPLE 1

Expression of Mutants for in vitro Work

The P450$_{cam}$ enzymes were expressed using the vector pRH1091 (Baldwin, J. E., Blackburn, J. M., Heath, R. J., and Sutherland, J. D. *Bioorg. Med. Chem. Letts.*, 1992, 2, 663–668.) which utilised the trc promoter (a fusion of the trp and lac promoters). This vector incorporates a strong ribosome binding site (RBS) and the gene to be expressed is cloned using an Nde I site on the 5' end of the gene. We used Hind III as the cloning site at the 3' end of the camC gene. The procedure for protein expression is as follows: Cells are grown at 30° C. until the OD$_{600\ nm}$ reaches 1.0–1.2, the temperature is increased to 37° C. and camphor added as a 1 M stock in ethanol to a final concetration of 1 mM. The culture is allowed to incubate at 37° C. for another 6 hours. The P450$_{cam}$ protein is expressed to high levels in the cytoplasm and the cells take on a red to orange-red colour.

We have also prepared a variant of pRH1091 (by PCR) which has a extra Xba I site between the RBS and the Nde I site. This is important because Nde I is not unique in M13, and this restriction site is also present in the reductase gene as well as the backbone of the pGLW11 vector used for the in vivo system. Xba I is unique in the polylinker region of M13, but absent in the genes of all three proteins in the P450$_{cam}$ system and in the expression vectors. It therefore allows the camC gene to be moved between the mutagenic and expression vectors.

How the Mutants were Made

Oligonucleotide-directed site-specific mutagenesis was carried out by the Kunkel method (Kunkel, T. A. *Proc. Natl. Acad. Sci. USA* 1985, 82, 488–492) using the Bio-Rad Mutagen kit. The recommended procedure is summarised as follows. An M13 mp19 subclone of the camC gene encoding P450$_{cam}$ (SEQ ID NO: 1) was propagated in the *E. coli* strain CJ236. This strain has the dut$^+$ung$^+$ phenotype and thus will tolerate the inclusion of uracil in place of thymine in DNA molecules. After three cycles of infection, uracil-containing single stranded (USS) M13 DNA was readily isolated by phenol extraction of mature M13 phage particles excreted into the growth medium. The mutagenic oligonucloetide (or oligonucleotides) were phosphorylated with T4 polynucleotide kinase and then annealed to the USS template. The four nucleotides, DNA polymerase, DNA ligase, ATP and other chemical components were added and the second strand was synthesised in vitro. The double stranded form thus obtained was transformed into the dut+ ung+ *E. coli* strain MV1190, which should degrade the uracil-containing template strand and propagate the mutant strand synthesised in vitro. Plaques were picked and phages of possible mutants grown in *E. coli* strains MV1190 or TG1. The single-stranded DNA from these were sequenced to determine whether the mutagenesis, reaction was successful. The mutagenic efficiency was 50–80%.

The mutant camC gene is excised from the M13 subclone by restriction digest with Nde I and Hind III, and the fragment of appropriate size is ligated to the backbone of the expression vector prepared by a similar Nde I/Hind III digest.

Multiple mutants were prepared either by further mutagenesis, also by the Kunkel method, or where the location of the sites in the sequence permits, simple cloning steps. There are two unique restriction sites within the camC gene which are absent from the expression vector. One is Sph I which spans residues 121–123, and the other is Sal I which spans residues 338 and 339. Therefore, all mutations at, for example, residues 87, 96, 98, and 101 are readily combined with mutations at higher number residues by ligating appropriate fragments from restriction digests of mutant camC genes with Nde I/Sph I and Sph I/Hind III and the backbone fragment from a Nde I/Sph I digest of the expression vector. Mutations at, for example, 395 and 396 can be similarly incorporated by digests in which Sph I is replaced with Sal I.

The rationale for introducing the unique Xba I site is now clear: many mutants with multiple mutations were prepared by the cloning procedure above. Without the Xba I site it would be impossible to clone the gene for these multiple mutants from the expression vector back into M13 for further rounds of mutagenesis. Of course these problems could be overcome by doing mutagenesis by PCR, for example.

EXAMPLE 2

| Substrate oxidation protocol: in vitro reactions | |
|---|---|
| Component | Final concentration |
| P450$_{cam}$ enzyme | 1 μM |
| Putidaredoxin | 10 μM |
| Putidaredoxin reductase | 1 μM |
| Bovine liver catalase | 20 μg/ml |
| KCl | 200 mM |
| Substrate | Typically 1 mM |
| NADH | 250–400 μM |

50 mM Tris-HCl buffer pH 7.4 is added to make up the volume.

Temperature controlled at 30° C., optional.

The NADH turnover rate could be determined by monitoring the absorbance at 340 nm with time.

Catalase does not catalyse the substrate oxidation reactions but rather it is present to remove any hydrogen peroxide by-product which could otherwise denature the P450$_{cam}$.

The method can be increased in scale to, for example, 20 ml total incubation volume to allow purification of sufficient products by HPLC for spectroscopic characterisation. Fresh substrate (1 mM) and NADH (1–2 mM) are added periodically, such as every 20 minutes in a total rection time of, typically, 3 hours.

EXAMPLE 3

The in vivo System

The in vivo systems were expressed using the vector pGLW11, a derivative of the plasmid pKK223 (Brosius, J. and Holy, A. *Proc. Natl. Acad. Sci. USA*, 1984, 81, 6929–6933). Expression is directed by the tac promoter and the vector incorporates a gene conferring resistance to the antibiotic ampicillin.

Two systems were constructed. The first one expressed the electron transfer proteins putidaredoxin reductase (camA gene) and putidaredoxin (camB gene) as a fusion protein with a seven amino acid peptide linker, and the P450$_{cam}$ enzyme (camC gene) was expressed by the same vector but it was not fused to the electron proteins. The second system expressed the three proteins as separate entities in the E. Coli host. Both systems were catalytically competent for substrate oxidation in vivo.

The general strategy was as follows. The genes for the three proteins were cloned using Eco RI and Hind III as flanking sites, with Eco RI at the 5' end. For both in vivo systems there are restriction sites between the genes, including between the reductase and redoxin genes in the fusion construct. These restriction sites were introduced by PCR, as detailed below. The first task, however, was to carry out a silent mutation to remove the Hind III site within the camA gene for the reductase. The AAGCTT Hind III recognition sequence in the came gene was changed to AAGCCT, which is a silent mutation because GCT and GCC both encode alanine. The gene was completely sequenced to ensure that there were no spurious mutations.

1. The Fusion Protein System 1.a Manipulation of the camA Gene by PCR

For the camA gene the primer below (SEQ ID NO: 5) was used at the 5' end of the gene to introduce the Eco RI cloning site and to change the first codon from GTG to the strong start codon ATG.

```
5'-GAG ATT AAG AAT TCA TAA ACA CAT GGG AGT GCG TGC CAT ATG AAC GCA AAC
       Eco RI     RBS        |→camA
```

At the 3' end of cam the primer (nucleotide sequence is SEQ ID NO: 7) was designed such that 15 bases are complementary to nucleotide sequence of the last five amino acid residues of camA. The stop codon immediately after the GCC codon for the last amino acid was removed, and then part of a seven amino acid linker (Thr Asp Gly Gly Ser Ser Ser; SEQ ID NO: 6) which contained a Bam HI cloning site (GGATCC=Gly Ser) was introduced. The coding sequence was thus (amino acid sequence is SEQ ID NO:8):

```
5'-GAA CTG AGT AGT GCC ACT GAC GGA GGA TCC TCA TCG-3'
       camA       →Thr Asp Gly Gly Ser
                                  |Bam HI|
```

The primer sequence shown below (SEQ ID NO: 9) is the reverse complement used for PCR:

5'-CGA TGA GGA TCC TCC GTC AGT GGC ACT ACT CAG TTC-3'

1.b Manipulations of the camB Gene by PCR

For the camB gene the primer at the 5' end (nucleotide sequence is SEQ ID NO: 10; amino acid sequence is SEQ ID NO: 11) incorporated the second half of the peptide linker between the reductase and redoxin proteins, and the restriction site Bam HI for joining the two amplified genes together.

```
5'-TCA TCG GGA TCC TCA TCG ATG TCT AAA GTA GTG TAT-3'
        Gly Ser Ser Ser|→ CamB
        |Bam HI|           Start
```

At the 3' end of camB the primer incorporates 12 nucleotides complementary to the end of camB followed by the stop codon TAA, a 6 nucleotide spacer before the GGAG ribosome binding site. Xba I and Hind III sites were then added to allow cloning of the camC gene when required. The sequence of the coding strand was therefore (SEQ ID NO: 12):

```
5'-CCC GAT AGG CAA TGG TAA TCA TCG GGAG TCT AGA GCA TCG AAG CTT TCA TCG-3'
                CamB →|stop      RBS Xba I Hind III
```

The primer shown below (SEQ ID NO: 13) is the reverse complement used for PCR:
5'-CGA TGA AAG CTT CGA TGC TCT AGA CTCC CGA TGA TTA CCA TTG CCT ATC GGG-3'

1.c Preparation of the Full Fusion Construct

The camA and camB genes were amplified by the PCR using the primers described above. The new camA was digested with Eco RI and Bam HI, while the new CamB was digested with Bam HI and Hind III. The pGLW11 expression vector was digested with Eco RI and Hind III. All three were purified by agarose gel electrophoresis and the three gel slices containing the separate fragments were excised from the gel and ligated together, and then transformed into E. Coli DH5α. Successful ligation of all the fragments were confirmed by a series of restriction digestion experiments, especially the presence of the new and unique Xba I site. The entire sequence of the insert from the Eco RI site to the Hind III site was determined to ensure that all the sequences were correct.

The new plasmid, named pSGB$^F$, was transformed into E. Coli and expression of the reductase and redoxin proteins was induced by IPTG. When a purified P450$_{cam}$ enzyme was added to the cell-free extract, substrate oxidation was observed for a variety of substrates.

When the camC gene is cloned into the pSGB$^F$ plasmid using the Xba I and Hind III restriction sites, the new recombinant plasmid thus generated expresses the reductase and redoxin as a fusion protein and the P450$_{cam}$ enzyme as a operate entity both from the same mRNA molecule. This in vivo system is catalytically competent for terpene oxidation in whole cells.

2. The in vivo System with the Protein Expressed Separately 2.a The Basic Strategy The starting point of the preparation of this in vivo system was the recombinant plasmid used to express the camA gene for putidaredoxin reductase. The camA gene was cloned into the pGLW11 plasmid using the Eco RI and Bam HI restriction sites, with Eco RI being at the 5' end of the gene. Conveniently the polylinker region of the pGLW11 vector has a Hind III site downstream of the Bam HI site. The camB gene was therefore manipulated by PCR such that it can be cloned into pGLW11 using the Bam HI and Hind III sites. This new plasmid expresses the reductase and redoxin as separate proteins.

The camB gene was cloned into pUC118 by the Bam HI and Hind III cloning sites to express putidaredoxin for our general in vitro substrate oxidation work. Therefore, the PCR primer at the 3' end of the camB gene was designed to introduce a ribosome binding site and the Xba I restriction site upstream of the Hind III site so that the camC gene can be inserted downstream of camB using the Xba I and Hind III sites. Therefore the three genes were cloned without fusion in the pGLW11 expression vector and arranged in the order 5'-camA-camB-camC-3', and each gene has its own RBS to initiate protein synthesis.

2.b Manipulations of the camB Gene

We used the internal and unique restriction site Mlu I (recognition sequence ACGCGT) within the camB gene as the starting point so that the PCR product has a different size from the PCR template fragment. The primers were as follows:

5'-TCA TCG ACG CGT CGC GAA CTG CTG-3' (SEQ ID NO: 14)

where the Mlu I site is in bold.

The desired coding sequence at the 3' end of the camB gene (SEQ ID NO:15) was:

```
5'-CCC GAT AGG CAA TGG TAA GTA GGT GAA TAT CTA ATC CCC ATC TAT GCG CGA GTG GAG TCT AGA GTT CGA-3'
       camB   →|stop                                                 RBS      Xba I
```

After the stop codon there is a 35 base spacer before the RBS which is used to initiate the synthesis of the P450$_{cam}$ enzyme. The Xba I cloning site is located within the spacer between the RBS and the start codon (not in this primer) of the camC gene. The PCR primer used was the reverse complement of the sequence above. The PCR was carried out and the amplified fragment of the appropriate size was purified by agarose gel electrophoresis and the gel slice excised.

One extra step was necessary to complete the construction of the new plasmid. The plasmid for the fusion protein in vivo system was digested with Mlu I and Hind III restriction enzymes, purified by agarose gel electrophoresis, and the gel slice for the small camB fragment excise. The pUC118 plasmid for camB expression was similarly digested, and the gel slice for the backbone was excised. By ligating the two fragments together we prepared a new pUC118-based plasmid which had an Xba I site followed by an Hind III site downstream of the stop codon of camB. This new plasmid was digested with the Mlu I and Xba I enzymes and the backbone was ligated with the new camB fragment described above to generate a plasmid with the following arrangement of the key components:

..lac Promoter..Bam HI..camB gene..spacer..RBS..Xba I..Hind III..

2.c Preparation of the in vivo System Plasmid

Once the modified camB with the Xba I and Hind III restriction sites and appropriate spacers were prepared, the in vivo system was constructed by cloning this into the pGLW11-based plasmid used to express the camA gene (reductase protein) using the Bam HI and Hind III sites. The new in vivo system vector has the following arrangement of the key components:

..tac Promoter..Eco IRI..RBS..camA gene..spacer..Bam HI..RBS..camB gene..spacer..RBS..Xba I..Hind III..

This new plasmid, named pSGB$^+$, was transformed into E. Coli and expression of the reductase and redoxin proteins was induced by IPTG. When a purified P450$_{cam}$ enzyme was added to the cell-free extract, substrate oxidation was observed for a variety of substrates.

When the camC gene is cloned into this pSGC$^+$ plasmid using the Xba I and Hind III restriction sites, the new recombinant plasmid thus generated will express the three proteins separately, each under the direction of its own RBS but from the same mRNA molecule. Thus constitutes the in vivo system used in the vast majority of our terpene oxidation work.

3. Introduction of an Xba I Site Into pRH1091

This is the final step to enable the camC gene to be cloned into the in vivo systems by the two cloning sites XbaI and Hind III. The Xba I site was added by PCR of the entire pRH1091 plasmid using two primers. The presence of these two sites will also enable cloning of the camC gene into M13 since both Xba I and Hind III are unique in camC and M13.

The primers shown below maintain the Hind III cloning site AAGCTT:

```
5'-TCA TCG AAG CTT GGC TGT TTT-3' (SEQ ID NO:16)
       Hind III|→ vector
```

At the other end the coding sequence desired was (SEQ ID NO: 17):

```
5'-ACA ATT TCA CAC AGGA TCT AGA C CAT ATG TCA TCG AAG CTT TCA TCG-3'
          Vector →|RBS XbaI    NdeI    Hind III
```

This sequence maintained the Nde I and Hind III sites but the new Xba I site was introduced upstream of the Nde I site. The PCR primer used was the reverse complement of the desired sequence (SEQ ID NO: 18):

5'-CGA TGA AAG CTT CGA TGA CAT ATG GTC T AGA TCCT GTG TGA AAT TGT-3'

The PCR product was then purified by agarose gel electrophoresis, digested with Hind III and circularised with T4 DNA ligase. Success of the PCR method was indicated by the presence of a new and unique Xba I site in plasmid DNA isolated from transformants.

4. Cloning of camC Into the in vivo Systems

All existing camC mutants were cut out of pRH1091-based expression plastids with Nde I and Hind III. The new vector is similarly cut with the same restriction enzymes and the camC gene cloned into this plasmid with T4 DNA ligase. This DNA is transformed into *E. Coli* JM109 which then may be grown to express $P450_{cam}$.

The camC gene is excised from the new vector using Xba I and Hind III restriction enzymes and cloned into either the in vivo vector systems or M13mp19 for mutagenesis.

5. In vivo Expression and Substrate Turnover

For protein expression, cells are grown in LBamp medium (tryptone 10 g/liter, yeast extract 5 g/liter, NaCl 10 g/liter, 50 µg/ml ampicillin) at 30° C. until the $OD_{600\ nm}$ reaches 1.0–1.2. IPTG (isopropyl-β-D-thiogalactopyranoside) was added to a final concentration of 1 µM (from a 1 M stock in $H_2O$) and the culture was incubated at 30° C. overnight.

For simple screening the substrate can be added to culture and the incubation continued. However, due to impurities from the culture media the cells were generally washed twice with 0.5 vol. of buffer P, ($KH_2PO_4$ 6.4 g, $K_2HPO_4 \cdot 3H_2O$ 25.8 g, $H_2O$ to 4 liters, pH 7.4) and resuspended in 0.25 vol. oxygen saturated buffer P containing 24 mM glucose. Substrate was added to 1 mM and the incubation continued at 30° C. The reaction was allowed to run for 24 hours with periodic additions of substrate and glucose.

EXAMPLE 4

The Oxidation of Halo Aromatic Compounds

The oxidation of halo aromatic compounds

| Mutant | 2,3,6-Trichlorophenol | 3,4,6-Trichlorophenol | Coupling Efficiency (%) | Product formation rate (min⁻¹) |
|---|---|---|---|---|
| Y96F | 75 | 25 | 18 | 22 |
| Y96A | 77 | 23 | 14 | 33 |
| Y96H | 54 | 46 | 3 | 1 |
| F87L-Y96F | 42 | 58 | 4 | 8 |
| F87A-Y96F | 52 | 48 | 2 | 3 |
| F87A-Y96-F-V247A | 43 | 57 | 4 | 7 |

| Mutant | 2,3-Dichlorophenol | 3,4-Dichlorophenol | Coupling Efficiency (%) | Product formation rate (min⁻¹) |
|---|---|---|---|---|
| Y96A | 94 | 6 | 6 | 19 |
| Y96F | 91 | 9 | 4 | 8 |
| Y96A-V247L | 94 | 6 | 7 | 20 |
| Y96L-V247A | 90 | 10 | 2 | 0.7 |
| F87L-96F | 96 | 4 | 3 | 5 |
| C334A | 95 | 5 | 2 | 0.5 |

All mutants have C334A. Coupling efficiency is the percentage of NADH consumed which was utilised for product formation, i.e. a percentage of the theoretical maximum efficiency. The product formation rates are given in (nmol product) $(nmol\ P450_{cam})^{-1}(min)^{-1}$. The relative amount of product formed in each case is shown. 1,3- and 1,4-dichlorobenzene, 1,2,3- and 1,3,5-trichlorobenzene, 1,2,4,5- and 1,2,3,5-tetrachlorobenzene, and 2,3,4,5,6- and 2,2',4,5,5'-pentachlorobiphenyl were also found to be oxidised.

Wild-type and mutant $P450_{cam}$ enzymes were tested for their ability to oxidise 3,3'-dichlorobiphenyl and 2,2',4,5,5'-pentachlorobiphenyl. Results are shown in terms of NADH turnover. Rates are given as nanomol NADH consumed per nanomol $P450_{cam}$ enzyme per minute.

| $P450_{cam}$ enzyme | 3,3'-dichlorobiphenyl | 2,2',4,5,5'-pentachlorobiphenyl |
|---|---|---|
| Wild-type | 0.4 | not detected |
| Y96F | 15 | 1 |
| F87A-Y96F | 845 | 165 |
| F87L-Y96F | 174 | 13 |
| F87W-Y96F | 4 | 3 |
| F87A-Y96F-V247A | 112 | 12 |
| Y96A-V247L | 84 | 37 |
| F87A-Y96F-L244A | 669 | 321 |
| F87A-Y97F-L244A-V247A | 173 | 214 |

The first product, 4-hydroxy-3,3'-dichlorobiphenyl was identified by the characteristic coupling patterns expected in the $^1H$ NMR spectrum and by mass spectroscopy. The further oxidation product, 4,4'-dihydroxy-3,3'-dichlorobiphenyl was identified by co-elution with an authentic sample, and by UV-vis and mass spectroscopy. This product did not constitute more than ca. 10% of the total products in any of the mutants tested.

For the second substrate product was established as 4'-hydroxy-2,2',4,5,5'-pentachlorobiphenyl by the observation of the parent ion in the mass spectrum, and by comparison with literature $^1H$ NMR data $P450_{cam}$ Mutants All mutants optionally contain the base mutation C334A.

Single mutants:

Y96A, Y96F, Y96L, Y96W.

Double mutants:

| | | | | |
|---|---|---|---|---|
| Y96A-F87A | Y96F-F87A | Y96F-V295A | Y96L-F87A | Y96L-A296L |
| Y96A-F87L | Y96F-F87I | Y96F-V295L | Y96L-F87L | Y96L-A296F |

-continued

| | | | | |
|---|---|---|---|---|
| Y96A-F87W | Y96F-F87L | Y96F-V295I | Y96L-F98W | Y96L-V396A |
| Y96A-F98W | Y96F-F87W | Y96F-A296L | Y96L-T101L | Y96L-V396L |
| Y96A-L244A | Y96F-F98W | Y96F-A296F | Y96L-T101F | Y96L-V396F |
| Y96A-V247A | Y96F-T101L | Y96F-I395F | Y96L-L244A | Y96L-V396W |
| Y96A-V247L | Y96F-T101F | Y96F-I395G | Y96L-L244F | |
| Y96A-I395F | Y96F-T185A | Y96F-V396A | Y96L-V247A | |
| Y96A-I395G | Y96F-T185F | Y96F-V396L | Y96L-V247L | Y96W-F87W |
| | Y96F-T185L | Y96F-V396F | Y96L-V247F | Y96W-F98W |
| | Y96F-L244A | Y96F-V396W | Y96L-V247W | Y96W-L244A |
| | Y96F-V247A | | Y96L-G248L | Y96W-V247A |
| | Y96F-V247L | | Y96L-V295L | Y96W-V396A |
| | Y96F-G248L | | Y96L-V295F | |

Triple Mutants:

| | | |
|---|---|---|
| Y96A-F87A-L244A | Y96L-V247A-V396L | Y96F-F87W-V247A |
| Y96A-F87A-V247A | Y96L-V247A-V396F | Y96F-F87W-V247L |
| Y96A-F87L-L244A | Y96L-V247A-V396W | Y96F-F87W-V247F |
| Y96A-F87L-V247A | Y96L-V247F-V396A | Y96F-F87W-V295L |
| Y96A-L244A-V247A | | Y96F-F87W-A296L |
| | Y96F-F87A-L244A | Y96F-F87W-V396A |
| Y96L-F87A-L244A | Y96F-F87A-V247A | Y96F-F87W-V396L |
| Y96L-F87A-V247A | Y96F-F87A-V247L | Y96F-V247F-V396A |
| Y96L-F87L-L244A | Y96F-F87A-I395F | Y96F-L244A-V396L |
| Y96L-F87L-V247A | Y96F-F87A-I395G | Y96F-L244A-V396F |
| Y96L-V247A-I395F | Y96F-F87L-V247A | Y96F-L244A-V396W |
| Y96L-V247L-I395F | Y95F-F87L-V247L | Y96F-L244F-V396A |
| Y96L-V247L-I395G | Y96F-F87L-I395F | Y96F-V247A-V396L |
| Y96L-L244A-V396L | Y96F-F87W-T185A | Y96F-V247A-V396F |
| Y96L-L244A-V396F | Y96F-F87W-T185F | Y96F-V247A-V396W |
| Y96L-L244A-V396W | Y96F-F87W-T185L | |
| Y96L-L244F-V396A | Y96F-F87W-L244F | Y96W-F87W-F98W |

Four mutations:

Y96A-F87A-L244A-V247A
Y96A-F87L-L244A-V247A
Y96L-F87A-L244A-V247A
Y96L-F87L-L244A-V247A
Y96F-F87W-L244A-V295L
Y96F-F87W-L244F-V396A
Y96F-F87W-L244A-A296L
Y96F-F87W-V247A-V396L
Y96F-F87W-V247A-V396F
Y96F-F87W-V247L-V295A
Y96F-F87W-V247L-V396A
Y96F-F87W-V247F-V396A
Y96F-F87W-V247A-I395F
Y96F-F87W-V247L-I395G

Five mutations:

Y96F-F87W-T185L-V247L-V295L
Y96F-F87W-T185L-V247L-V396A
Y96F-F87W-T185L-V247L-V396L

What is claimed is:

1. A process for oxidizing a substrate which is 1,2-dichlorobenzene, 1, 2, 4-trichlorobenzene, 3, 3'-dichlorobiphenyl, 2, 2', 4, 5, 5'-pentachlorobiphenyl, pentachlorobenzene or hexachlorobenzene, said process comprising the step of oxidizing said substrate with a mutant P450 monooxygenase enzyme in the presence of an electron transfer reductase and an electron transfer redoxin, wherein the enzyme is a P450cam enzyme as shown by SEQ ID NO:2, comprising a mutation at one or more of the amino acid positions selected from the group consisting of 87, 96, 98, 101, 185, 244, 247, 248, 295, 296, 395 and 396, and wherein the mutation is a substitution of an amino acid with an amino acid that has a less polar side chain, and further wherein a ring carbon of the substrate is oxidised in the oxidation reaction.

2. The process of claim 1 in which the enzyme comprises a mutation at more than one of said amino acid positions.

3. The process of claim 1 in which the enzyme comprises a mutation at amino acid 96 of $P450_{cam}$.

* * * * *